US010189761B2

(12) United States Patent
Curtis et al.

(10) Patent No.: US 10,189,761 B2
(45) Date of Patent: Jan. 29, 2019

(54) METHOD FOR POLYOL SYNTHESIS FROM TRIACYLGLYCERIDE OILS (71) Applicant: THE GOVERNORS OF THE UNIVERSITY OF ALBERTA, Edmonton (CA)

(72) Inventors: Jonathan M. Curtis, Edmonton (CA); Tolibjon S. Omonov, Edmonton (CA); Ereddad Kharraz, Edmonton (CA); Xiaohua Kong, Edmonton (CA); Hossein M. Tavassoli-Kafrani, Edmonton (CA)

( * ) Notice: Subject to any disclaimer, the term of this patent is extended or adjusted under 35 U.S.C. 154(b) by 0 days.

(21) Appl. No.: 15/736,999

(22) PCT Filed: Jun. 27, 2016

(86) PCT No.: PCT/CA2016/050753
§ 371 (c)(1),
(2) Date: Dec. 15, 2017

(87) PCT Pub. No.: WO2016/205958
PCT Pub. Date: Dec. 29, 2016

(65) Prior Publication Data
US 2018/0170845 A1 Jun. 21, 2018

Related U.S. Application Data (60) Provisional application No. 62/183,982, filed on Jun. 24, 2015.

(51) Int. Cl.
C07C 29/48 (2006.01)
C07C 67/31 (2006.01)
(Continued)

(52) U.S. Cl.
CPC ............ *C07C 29/48* (2013.01); *B01J 31/0212* (2013.01); *B01J 41/08* (2013.01); *C07C 29/1285* (2013.01);
(Continued)

(58) Field of Classification Search
CPC ... C07C 29/48; C07C 29/1285; C07C 31/205; C07C 29/132; C07C 67/02; C11C 3/006
See application file for complete search history.

(56) References Cited

U.S. PATENT DOCUMENTS 9,216,940 B2 * 12/2015 Curtis ................. C07C 67/31
2010/0197878 A1 * 8/2010 Casati ................ C08G 18/3206
526/319

(Continued)

FOREIGN PATENT DOCUMENTS

EP 0743334 * 11/1996
GB 1100404 * 1/1968

OTHER PUBLICATIONS

Lozada, Z., et al., Soy-based polyols from oxirane ring opening by alcoholysis reaction, 2009, Journal of Applied Polymer Science, vol. 113, pp. 2552-2560 (Year: 2009).*

Primary Examiner — Yate' K Cutliff
(74) Attorney, Agent, or Firm — Bennett Jones LLP (57) ABSTRACT A method for preparation of polyols from an unsaturated TAG oil that involves first epoxidizing the unsaturated TAG oil; then subjecting the epoxidized TAG oil to transesterification using a diol and/or triol in the presence of a catalyst to produce hydroxyalkyl esters of fatty acid epoxides; and finally hydroxylating the transesterification product using a diol and/or triol and a solid acid catalyst to obtain a polyol with relatively high hydroxyl value and low viscosity.

18 Claims, 5 Drawing Sheets (51) Int. Cl.
  *C08G 18/36*   (2006.01)
  *C11C 3/00*    (2006.01)
  *B01J 31/02*   (2006.01)
  *B01J 41/08*   (2017.01)
  *C07C 29/128*  (2006.01)
  *C07C 31/20*   (2006.01)
  *C11C 3/06*    (2006.01)
  *C07D 301/12*  (2006.01)
  *C07C 29/132*  (2006.01)
  *C07C 67/02*   (2006.01)

(52) U.S. Cl.
  CPC ............ *C07C 31/205* (2013.01); *C07C 67/31* (2013.01); *C07D 301/12* (2013.01); *C08G 18/36* (2013.01); *C11C 3/003* (2013.01); *C11C 3/006* (2013.01); *C11C 3/06* (2013.01); *C07C 29/132* (2013.01); *C07C 67/02* (2013.01)

(56) References Cited

U.S. PATENT DOCUMENTS

2010/0240860 A1*  9/2010  Abraham ................ C07C 67/03
                                                  528/361
2013/0274494 A1* 10/2013  Curtis ..................... C07C 67/31
                                                  554/172

\* cited by examiner

METHOD FOR POLYOL SYNTHESIS FROM TRIACYLGLYCERIDE OILS

FIELD OF THE INVENTION

The present invention relates to a process for the preparation of polyols from unsaturated triacylglycerol oil.

BACKGROUND OF THE INVENTION

In polymer chemistry, polyols are compounds with multiple hydroxyl functional groups available for chemical reactions. A major use of polyols is as a reactant to make polymers. Polyols may also be used for other purposes including in cosmetic formulations, lubricants and as chemical intermediates. Polyols themselves may be monomeric, oligomeric or polymeric. The ability to produce polyols of different molecular weights is desirable since these can be used to produce polymer networks with different properties. Monomeric or oligomeric polyols may be polymerized, for example into polyesters or polyethers, before conversion to other polymers such as polyurethanes.

Polyol production from renewable, non-petroleum based sources is desirable from a sustainability perspective. Methods are known for the preparation of polyols from vegetable oil, typically involving harsh reaction conditions that are not easily controlled, and using expensive starting materials and catalysts. Natural oils or fatty acids may be oxidized by ozonolysis, or epoxidized with peroxy acids, followed by hydroxylation to produce polyols.

A process for preparing polyol from fatty acid substrates such as free fatty acids, alkyl esters of fatty acids, monoglycerides, diglycerides, and triglycerides is disclosed in United States Patent Application Publication No. 2013/0274494. The process involves epoxidizing the fatty acid substrate and then hydroxylating the epoxidized unsaturated substrate with at least one diol to produce a polyol or a blend of polyols. While the epoxidation of unsaturated oils proceeds well under optimized epoxidation conditions without loss of the epoxy groups, the epoxidation of the fatty acid methyl esters (FAMEs) and free fatty acids mixtures (FFAs) show extensive loss of epoxy groups (hence epoxy functionality) due to premature epoxy ring opening under acid attack and/or due to the oligomerization processes occurred during epoxidation.

Accordingly, there is a need in the art for improved or alternative processes of preparing polyols.

SUMMARY OF THE INVENTION

The invention relates to a process for the preparation of polyols from unsaturated triacylglycerol (TAG) oil.

In one aspect, the invention comprises a method for the preparation of polyols from an unsaturated TAG oil, comprising the steps of:
 (a) fully or partially epoxidizing the unsaturated TAG oil to obtain epoxidized TAG oil;
 (b) transesterifying the epoxidized TAG oil using a diol and/or a triol in the presence of a catalyst and a solvent, to produce hydroxyalkyl esters of fatty acid epoxides; and
 (c) hydroxylating the transesterification product using a diol and/or triol and a catalyst to obtain polyols.
Preferably, the catalyst in step (c) is a solid acid catalyst.

In one embodiment, the unsaturated TAG oil comprises canola oil, high oleic canola oil, sunflower oil, juvenile canola oil, flax oil, camelina oil, solin oil, yellow mustard oil, brown mustard oil, oriental mustard oil, palm oil olein, palm oil, palm kernel oil, soy oil, high erucic acid rapeseed oil, hemp oil, corn oil, olive oil, peanut oil, safflower oil, cottonseed oil or mixtures thereof.

In one embodiment, in step (a), unsaturated TAG oil is epoxidized by any suitable method, such as with formic acid and an oxidizing agent or with a chemo-enzymatic method. In one embodiment, the oxidizing agent comprises hydrogen peroxide. In one embodiment, the unsaturated TAG oil is mixed with the oxidizing agent at a temperature of about from about 20° to about 40° C., more preferably from 20° to about 30° C. In one embodiment, the temperature is then gradually increased to about 40° to about 60° C. as the acid is added slowly. In one embodiment the epoxidation of the unsaturated TAG oil is catalyzed by an enzyme, such as lipase. In one embodiment, the epoxidized TAG oil is extracted using an organic solvent and dried.

In one embodiment, in step (b) and/or (c), the diol and/or triol comprises 1,2-propane diol, 1,3-propane diol, 1,4-butane diol, ethylene glycol, glycerol, glycerol acetates, or mixtures thereof. In one embodiment, the diol comprises 1,3-propane diol.

In one embodiment, in step (b) the catalyst comprises an alkoxide. In one embodiment, the alkoxide comprises anhydrous sodium methoxide, dissolved in a suitable solvent, such as acetone. In one embodiment, the epoxidized TAG oil is mixed with the catalyst solution and the diol and/or triol at a temperature of about 40° to about 70° C., and more preferably about 50° to about 60° C. In one embodiment, the catalyst is neutralized by addition of a mineral acid or an acid immobilized onto a solid support, such as beads. In one embodiment, the acid immobilized solid beads comprises a heterogeneous macroreticular ion exchange resin operating in strong anion exchange mode.

In one embodiment, in step (c), the solid acid catalyst comprises a heterogeneous macroreticular ion exchange resin. In one embodiment, the solid acid catalyst is added to a mixture of the epoxidized unsaturated TAG and the diol or the triol once the mixture has reached a temperature of about 60° C.

In one embodiment, the method produces polyols having a hydroxyl value of greater than about 340 mg KOH/g, with a viscosity no greater than about 2.0 Pa·s at 25° C. In another embodiment, the method produces polyols having a hydroxyl value of greater than about 405 mg KOH/g, with a viscosity no greater than about 8 Pa·s at 25° C.

In another aspect, the invention may comprise polyol produced from an unsaturated TAG oil by the sequential steps of epoxidation, transesterification and hydroxylation, which polyol has a hydroxyl value greater than about 340 KOH/g with a viscosity no greater than about 8.0 Pa·s at 25° C.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION OF PREFERRED EMBODIMENTS

Figure 1:
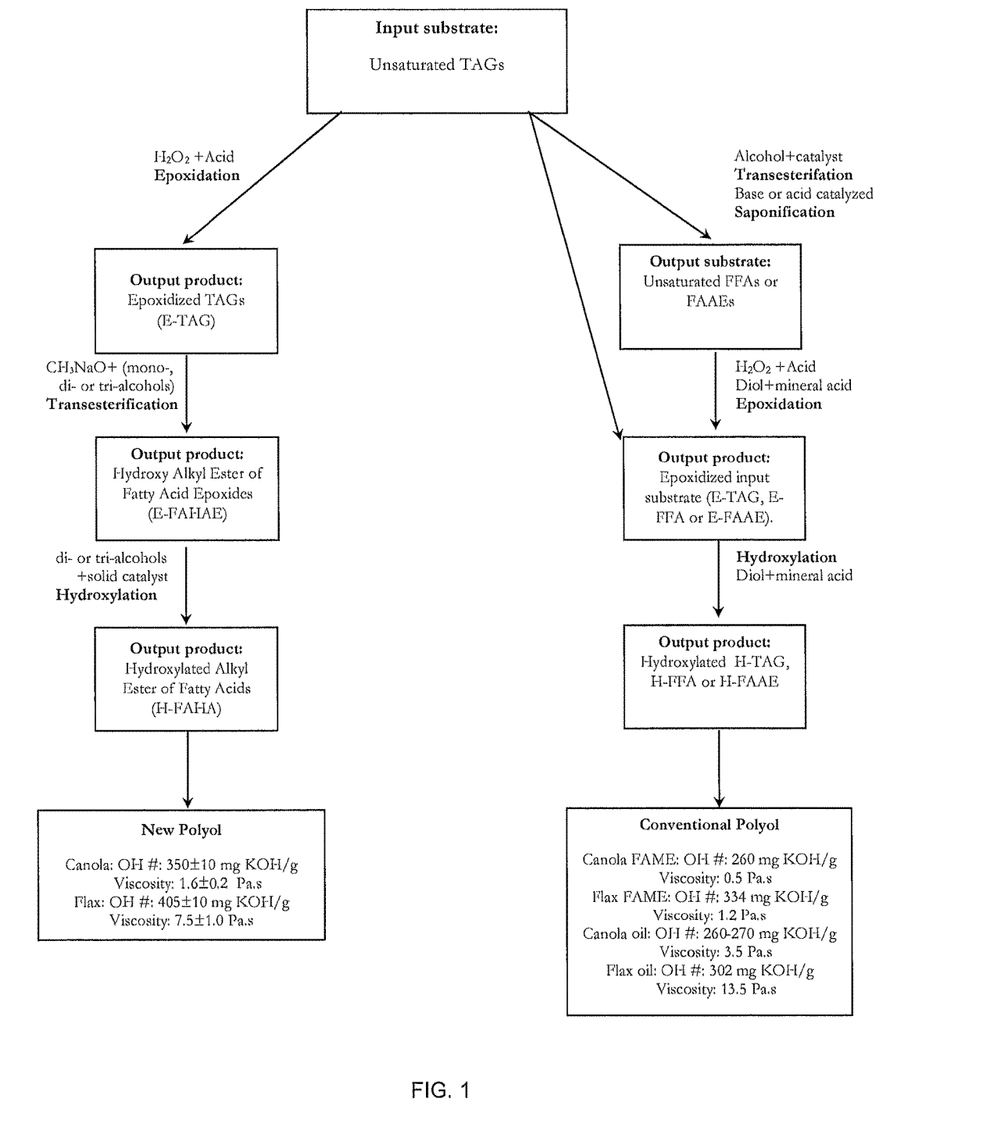
FIG. 1 compares reaction schemes of a prior art process (right) and one embodiment of the process of the present invention (left), showing the hydroxyl value (OHV) and viscosity of exemplary resultant polyols.

The present invention comprises a process wherein diols and/or triols are used to transesterify epoxidized TAGs to produce hydroxyalkyl esters of fatty acid epoxides, and subsequently used to ring open these hydroxyalkyl esters of fatty acid epoxides to produce polyols. The resultant polyols may have enhanced hydroxyl functionality. FIG. 1 generally compares the reaction schemes of a prior art process and one embodiment of the process of the present invention, showing the hydroxyl value ("OHV") and viscosity of the resulting polyols.

Figure 2:
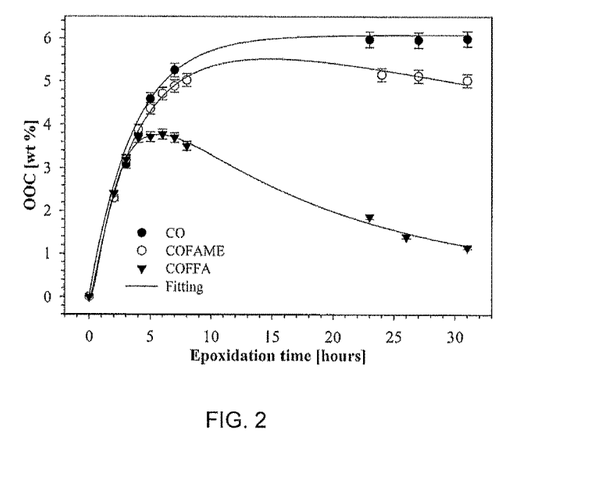
FIG. 2 is a graph comparing kinetics of epoxidation (oxirane oxygen content expressed as wt %, OOC) for canola oil (CO), canola oil fatty acid methyl esters (COFAMEs) and canola oil free fatty acids (COFFAs) at 60° C.

While the epoxidation of unsaturated oils proceeds well under optimized epoxidation conditions without loss of the epoxy groups, the epoxidation of the fatty acid methyl esters ("FAMEs") and free fatty acids mixtures ("FFAs") show extensive loss of epoxy groups (hence epoxy functionality) due to unwanted epoxy ring opening under acid attack and/or due to the oligomerization processes occurred during epoxidation. FIG. 2 shows the kinetics of epoxidation of canola oil (CO), canola oil fatty acid methyl esters (COFAME) and canola oil free fatty acids (COFFA) through the change of the oxirane oxygen content ("OOC") during epoxidation periods. Without restriction to a theory, it appears that epoxidation of oil proceeds to a greater extent compared to epoxidation of its derivatives (COFAMEs and COFFAs). Thus, epoxidized oil has higher final values of OOC compared to its derivatives. These different epoxidation behaviors of unsaturated oils and their derivatives may be attributed to basic structural differences. Epoxy groups of FAMEs and FFAs are more susceptible to ring opening due to the presence of organic acids, while epoxy ring opening of the epoxidized oil may be retarded due to greater steric hindrance or other reasons. Without restriction to a theory, the relatively lower OOC in the case of epoxidized oil derivatives may be explained by the enhanced ring opening of oxirane by added carboxylic acid (e.g. formic acid) and by fatty acids themselves (in case of FFA epoxidation) to form a variety of structures, for example the formation of a secondary hydroxyl group with adjacent formoxy pendant group.

Figure 3:
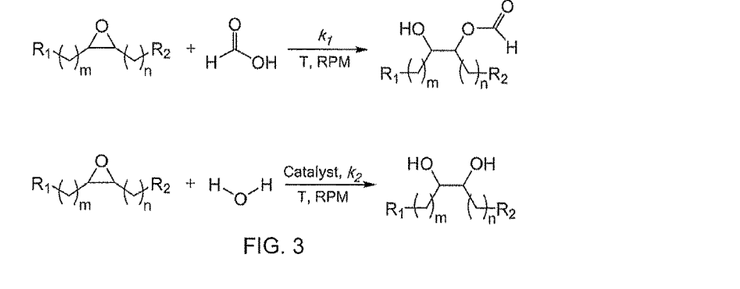
FIG. 3 show examples of epoxy ring opening: formic acid (top) and water (bottom).
Figure 4:
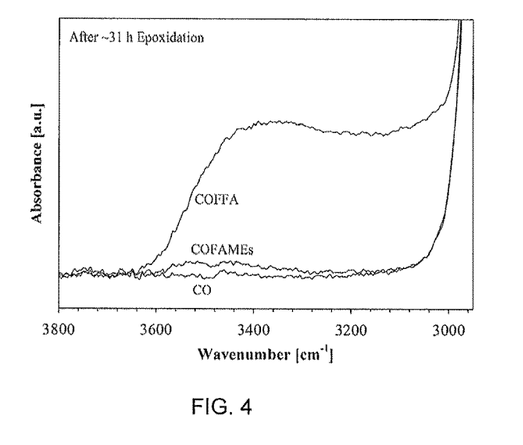
FIG. 4 shows a region of the FTIR spectra that illustrates the extent of hydroxyl group formation in CO, COFAMEs and COFFAs after epoxidation at 60° C. for 31 hours.

The reaction may also involve fatty acids or/and the oligomers of the fatty acids (estolides). FIG. 3 shows examples of epoxy ring opening by components present in epoxidation. FIG. 4 shows evidence of epoxy ring opening in canola oil derivatives via the FTIR spectra, which give a qualitative estimation of hydroxyl group formation during the epoxidation of canola oil and its derivatives due to the premature epoxy ring opening. The nearly flat plateau region of the canola oil (CO) FTIR spectra in the range of about 3000-3600 $cm^{-1}$ indicates that few or no hydroxyl groups were formed after 31 hours of epoxidation (FIG. 4).

Compared to the prior art, the process of the present invention may allow for the preparation of epoxidized derivatives of vegetable oils and animal fats, while reducing loss of epoxy functionality. It is well known that epoxy ring opening during epoxidation leads to the formation of the secondary hydroxyl groups which are less reactive. Embodiments of the present invention may minimize formation of secondary hydroxyl groups during epoxidation by minimizing epoxy ring opening. High OOC of the epoxidized product provides a base for increased hydroxyl functionality, as avoiding premature ring opening by carboxylic acid eliminates formation of formates (if formic acid is used as the oxygen carrier). Embodiments of the present invention may protect well-balanced primary and secondary hydroxyl groups from epoxy ring opening. In one embodiment, the expected ratio of primary to secondary hydroxyl groups from epoxy ring opening of epoxides due to esterification of diol is about 1:1.

In one embodiment, the invention comprises a method for the preparation of polyols from unsaturated TAG oil having at least one, preferably two or more, C—C double bond, comprising the steps of:

(a) epoxidizing the unsaturated TAG oil to obtain an epoxidized TAG oil;

(b) transesterifying the epoxidized TAG oil using a diol and/or triol in the presence of a catalyst and a solvent, to produce hydroxyalkyl esters of fatty acid epoxides; and (c) hydroxylating the transesterification product using a diol and/or triol and a solid acid catalyst to obtain a polyol or blend of polyols.

Any TAG oil containing unsaturated fatty acid chains can be used as starting material. Those oils with higher degrees of unsaturation such as canola oil, high oleic canola oil, sunflower oil, flax oil, solin oil, yellow mustard oil, brown mustard oil and oriental mustard oil, camelina oil, palm oils, palm kernel oil, soy oil, high erucic acid rapeseed oil, hemp oil, corn oil, olive oil, peanut oil, safflower oil, cottonseed oil, or fractionated oils for example, palm oil olein, may be preferred. Edible oils which are fully refined, (for example, degummed, bleached, deodorised) can be used as can non-refined oils that may not be food grade, such as juvenile or "green" canola, camelina oil, high erucic acid rapeseed oil. Use of different oils with different triglyceride compositions, when fully or partially epoxidized, will result in different polyols, molecular weights, hydroxyl numbers, and viscosities giving access to a wide variety of polyols for various purposes.

In one embodiment, the epoxidation step of the unsaturated TAG oil involves reaction with an oxidizing agent, such as hydrogen peroxide, catalyzed by a carboxylic acid, such as formic acid. In one embodiment, the carboxylic acid is slowly added to a well-stirred emulsion of the unsaturated TAG oil and hydrogen peroxide. In one embodiment, the emulsion is formed by mixing the unsaturated TAG oil with hydrogen peroxide at a temperature of about 20° to about 40° C., preferably from 20° to about 30° C. The temperature is then gradually increased to about to about 40° to about 60° C. as the carboxylic acid is added slowly. The reaction may then proceed with vigorous mixing until the C—C double bonds of TAG are partially or wholly consumed. The reaction is stopped and the epoxidized TAG oil is separated from the mixture. This could be achieved by extraction with an organic solvent (such as, for example, ethyl acetate), followed by aqueous washes. Alternatively, separation of epoxidized TAG oil can be achieved without use of solvent, for example, by centrifugation or by distillation methods. The oxirane oxygen content ("OOC" expressed as weight percent) and hydroxyl value ("OHV" expressed as mg KOH/g) of dried epoxidized TAG oil may be determined using any conventional techniques which are well known to those skilled in the art.

In one embodiment, the transesterification step involves reaction of the epoxidized TAG oil with a diol and/or triol, in the presence of a catalyst and a solvent. Suitable diols or triols may include 1,2-propane diol, 1,3-propane diol, 1,4-butane diol, ethylene glycol, glycerol, glycerol acetates, or mixtures thereof, and may also include mixtures of two or more reactive alcohols, for example, mixtures of 1,2-propane diol and 1,3-propane diol. In one embodiment, the diol comprises 1,3-propane diol.

In one embodiment, the catalyst comprises an alkoxide, such as sodium methoxide, dissolved in a suitable solvent. To help avoid premature ring opening during transesterification, freshly prepared anhydrous alkoxide may be used.

In one embodiment, the epoxidized TAG oil is mixed with sodium methoxide solution and the diol and/or triol at a temperature of about 40° to about 70° C., and more preferably about 50° to about 60° C. In one embodiment, anhydrous sodium methoxide is dissolved in acetone. In one embodiment, the epoxidized TAG is mixed with sodium methoxide solution and the diol and/or triol for between about two to about six hours, preferably about four hours. The reaction may be stopped by addition of an acid to neutralize the catalyst. In one embodiment, the acid may comprise a mineral acid such as sulfuric acid, or an acid immobilized on a solid support, such as solid beads. Preferably, the solid beads comprise a heterogeneous macroreticular ion exchange resin operating in strong anion exchange mode. Following the reaction, the solvent may be removed by evaporation.

In the prior art, fatty acid alkyl ester epoxides were prepared from oleic acid using a monohydric alcohol (i.e., containing one hydroxyl group) such as, for example, methanol. After transesterification, there is no alcohol group as shown in formula (I) below:

methyl 8-(3-octyloxiran-2-yl)octanoate

In one embodiment of the method of the present invention, hydroxyalkyl esters of fatty acid epoxides are prepared from epoxidized TAG oil via a transesterification reaction. Each epoxidized TAG molecule yields three fatty acid hydroxyalkyl esters, each with a primary alcohol moiety after transesterification. For example, formula (II) shows an example of a hydroxyalkyl ester of a fatty acid epoxide, resulting from the transesterification of epoxidized triolein. Primary alcohols are preferred for their reactivity for particular applications such as, for example, the production of polyurethane.

3-hydroxypropyl 8-(3-octyloxiran-2-yl)octanoate

The transesterification product may then be further hydroxylated in an epoxide ring opening step with a diol and/or triol, and an acid catalyst. An epoxide group is comprised of two adjacent carbon atoms bridged by an oxygen atom. Ring opening of an epoxide group by a diol, for example 1,3 propanediol, results in the formation of a secondary hydroxyl group at one carbon and a hydroxyalkyl ether group at the other. Hence, in the case of hydroxylation by 1,3 propanediol, every epoxide group on the epoxidised fatty acid hydroxyalkyl esters gives rise to both a primary and a secondary hydroxyl group. In addition, there is a further primary hydroxyl group on the hydroxyalkyl ester site. Thus, a polyol resulting from a hydroxyalkyl ester containing one epoxide group (e.g. originating from oleic acid) would have three hydroxyl groups, two of which are primary. Similarly, a polyol resulting from a hydroxyalkyl ester containing two epoxide groups (e.g. originating from linoleic acid) would have five hydroxyl groups, three of which were primary. Many variations are possible depending on the starting oil and the diol and/or triol chosen. In one embodiment, polyol resulting from hydroxylation with 1,3-propane diol, may comprise structures similar to the examples shown in Formulas (III) and (IV) below:

3-hydroxypropyl 9-hydroxy-10-(3-hydroxypropoxy)octadecanoate (III)

3-hydroxypropyl 10,13-dihydroxy-9,12-bis(3-hydroxypropoxy)octadecanoate (IV)

These illustrated examples are not the only structures which will be produced. For example, the resulting polyols may include positional isomers of the these structures. Different positions of the double bond(s) in the substrate fatty acid moiety will lead to other structures as well.

Thus, hydroxylation of the hydroxyalkyl fatty acid epoxides produces a blend of polyols having available primary and secondary hydroxyl groups at the double bond site or sites of the TAG, and a primary hydroxyl group at the carboxylic acid site.

In one embodiment, the hydroxylation catalyst comprises a solid acid catalyst, such as a heterogeneous macroreticular ion exchange resin. Preferably, the resin comprises beads with high porosity, ranging from about 30% to about 50% and high surface area, ranging from about 45 $m^2/g$ to about 65 $m^2/g$, to expose reactive groups and sulfonic acid functionality. Commercially available catalysts such as Amberlyst™ 15 may be suitable. Use of a safer, heterogeneous solid catalyst and an alcohol may help prevent undesirable ring opening which typically occurs from use of a hazardous, homogeneous acidic catalyst or acidic aqueous medium.

In one embodiment, the solid acid catalyst is added to a mixture of the transesterification product and the diol and/or triol once the mixture has reached a temperature of about 40° C. to about 70° C., preferably about 60° C. In one embodiment, the mixture is agitated for about four to about eight hours, preferably about six hours. In one embodiment, the hydroxylation times of transesterification product using the 15% w/w of the heterogeneous catalyst was found to be comparable to the prior art process using sulfuric acid catalyst.

After the reaction has completed, the polyols may be extracted by addition of an organic solvent (such as, for example, ethyl acetate) and washed with saturated salty water. Any remaining water is removed by adding sodium sulfate. The ethyl acetate may be removed by evaporation. Any unreacted, excessive alcohol (for example, glycerol may be generated) is separated from the polyol using a low pressure wiped film evaporator or the like, and reused for further hydroxylation processes without purification.

Following hydroxylation, the solid acid catalyst may be easily replaced in the reactor or removed by filtration, eliminating the need for solvents (i.e., ethyl acetate and water) typically required for work-up and decreasing manufacturing costs. Depending upon its reactivity, the solid catalyst may be re-used for multiple hydroxylation cycles.

The polyols of the present invention may be used in polymer chemistry in the same manner as known polyols.

The method of the present invention may allow epoxidation of the unsaturated TAG to occur with reduced or minimal loss of epoxy groups, and may enable the functionality of polyols to be optimized towards specific applications. The functionality can be better controlled up to about the maximum possible OHVs, compared to the prior art process. For example, the OHVs of polyols used to produce rigid foams is very high, whereas the OHVs of polyols used to produce flexible foams is low.

During hydroxylation, epoxides are converted into the desired polyols (hydroxylated fatty acid alkyl esters—H-FAHA in FIG. 1). In one embodiment, the OHV of the polyols produced from canola oil is about 350 mg KOH/g, compared to 260-270 mg KOH/g for the prior art canola oil polyols, while the viscosity of the polyols is about 1.6 Pa·s compared to about 3.5 Pa·s for the prior art canola oil polyol. In another embodiment, the OHV of the polyol produced from flax oil is about 405 mg KOH/g, compared to 302 mg KOH/g for the prior art flax oil polyol, while the viscosity of the polyol is about 7.5 Pa·s compared to about 13.5 Pa·s for the prior art flax FAME polyol. Therefore, the polyols produced by methods of the present invention have higher hydroxyl values and lower viscosity than polyols produced using a prior art process which does not seek to minimize premature epoxide ring opening (FIG. 1).

In one embodiment, different types of polyhydric alcohols can be used for transesterification. For example, short chain, long chain, branched chain, aromatic or cyclic diols or triols may be used to prepare epoxidized, hydroxylated fatty acid esters. Alternative polyhydric alcohols may be immiscible with lipids/lipid derivatives and thus may require use of solvents. For example, the preparation of epoxides of fatty acid esters can be carried out in a suitable solvent to overcome immiscibility or solubility issues of alkali metal alkoxides with the reactants.

Exemplary embodiments of the present invention are described in the following Examples, which are set forth to aid in the understanding of the invention, and should not be construed to limit in any way the scope of the invention as defined in the claims which follow thereafter. As will be apparent to those skilled in the art, various modifications, adaptations and variations of the specific disclosure herein can be made without departing from the scope of the invention claimed herein.

Example 1—Epoxidation

Canola oil (1.0 kg) was transferred to a reactor (12 liter) equipped with an agitator motor and heating system. Hydrogen peroxide (35%, 0.618 kg) was transferred to the reactor and the temperature set to 30° C. The mixture was agitated at 300 rpm. Formic acid (61.5 g) was added dropwise to the reactor. When the entire formic acid was added, the temperature was increased to 60° C. at a rate of 5° C. per each 10 minutes. The reaction was continued for about 36 h. After completion of epoxidation, the product was extracted by adding ethyl acetate (1.0 L) and washing four times with saturated salty water. The solution was dried by adding sodium sulfate (0.25 kg) and the solvent was removed using a rotary evaporator under vacuum. The product was stored at room temperature. The oxirane oxygen content (%) and hydroxyl value (OHV, mg KOH/g) of epoxidized canola oil, epoxidized canola fatty acid methyl ester and canola free fatty acids are compared in Table 1. Epoxidation of the fatty acid methyl esters (FAMEs) and free fatty acids (FFAs) result in loss of epoxy groups due to enhanced epoxy ring opening, yielding a lower oxirane content with increased OHV (FIG. 2). For canola oil, epoxidation yields a maximum oxirane content with minimum OHV.

TABLE 1

Oxirane oxygen content (%) and hydroxyl value (mg KOH/g) of epoxidized canola oil, epoxidized canola FAME and epoxidized canola FFA.

|  | OOC[†] [%] | OHV[†] [mg KOH/g] |
|---|---|---|
| Epoxidized Canola Oil | 5.9 ± 0.2 | 8.8 ± 2.2 |
| Epoxidized Canola FAME | 5.2 ± 0.2 | 34.8 ± 1.0 |
| Epoxidized Canola FFA | 1.2 ± 0.1 | 234.9 ± 0.7 |

[†]OOC and OHV are measured after 31 hours of epoxidation at 60° C.

Example 2—Transesterification

Figure 5:
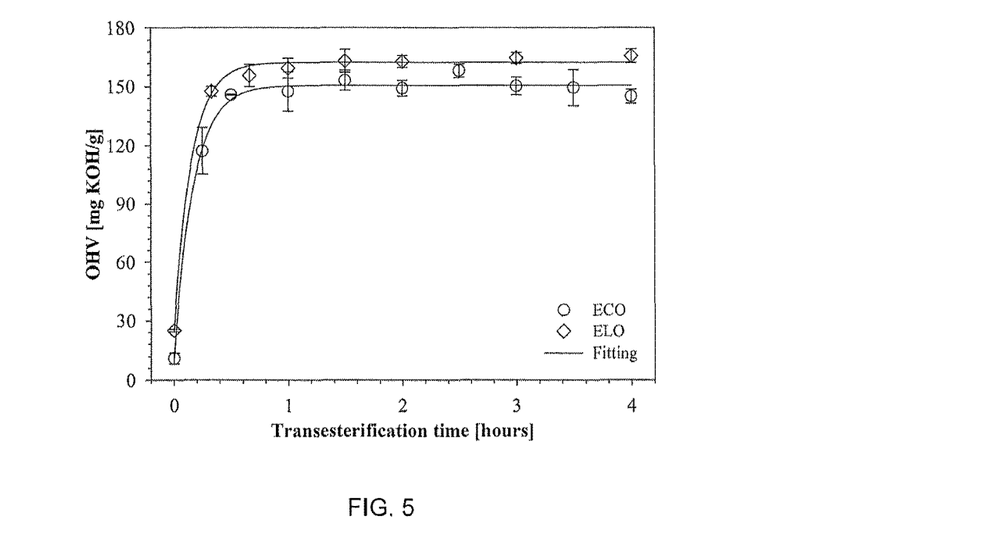
FIG. 5 is a graph showing hydroxyl value (mg KOH/g) of transesterified (with 1,3-propane diol (PDO)) derivatives of epoxidized canola (open circle symbols) and epoxidized flax (open diamond symbols) over transesterification time (hours).

Epoxidized canola oil (1.0 kg) or epoxidized flax oil prepared as described in Example 1 was transferred into a reactor (12 liter) equipped with an agitator motor and heating system, with the temperature set to 60° C. Sodium methoxide (95%, 10.0 g) dissolved in acetone (0.5 kg) and 1,3-propanediol (0.8 kg) were mixed for about 2 minutes and transferred into the reactor to mix with the epoxidized oil at 300 rpm. After 4 hours of the reaction, sulfuric acid (98%, 9.2 g) was added dropwise to the mixture to neutralize sodium methoxide. Acetone was removed using a rotary evaporator under vacuum. After removing acetone, the remaining material was returned back to the reactor. Oxirane content (%) and the hydroxyl values (mg KOH/g) of the transesterified products of epoxidized canola and epoxidized flax were determined (Table 2). FIG. 5 is showing hydroxyl value of transesterified (with 1,3-PDO) derivatives of epoxidized canola (open circle symbols) and epoxidized flax (open diamond symbols) over transesterification time. Note that both transesterified products from epoxidized canola and epoxidized flax oils should have similar OHV; however, observed higher OOC for the epoxidized flax derivatives are due to the higher OHV of input epoxidized flax oil occurred during epoxidation process and is not likely related to the transesterification process.

TABLE 2

Oxirane content (%) and OHV (mg KOH/g) of epoxidized canola oil and epoxidized flax oil after transesterification with 1,3-propanediol.

| Transesterified product of: | OOC[†] [%] | OHV[†] [mg KOH/g] |
|---|---|---|
| Epoxidized Canola Oil | 5.2 ± 0.2 | 150.5 ± 4.2 |
| Epoxidized Flax Oil | 7.8 ± 0.2 | 163.2 ± 2.4 |

[†]OOC and OHV are an average values

Figure 6:
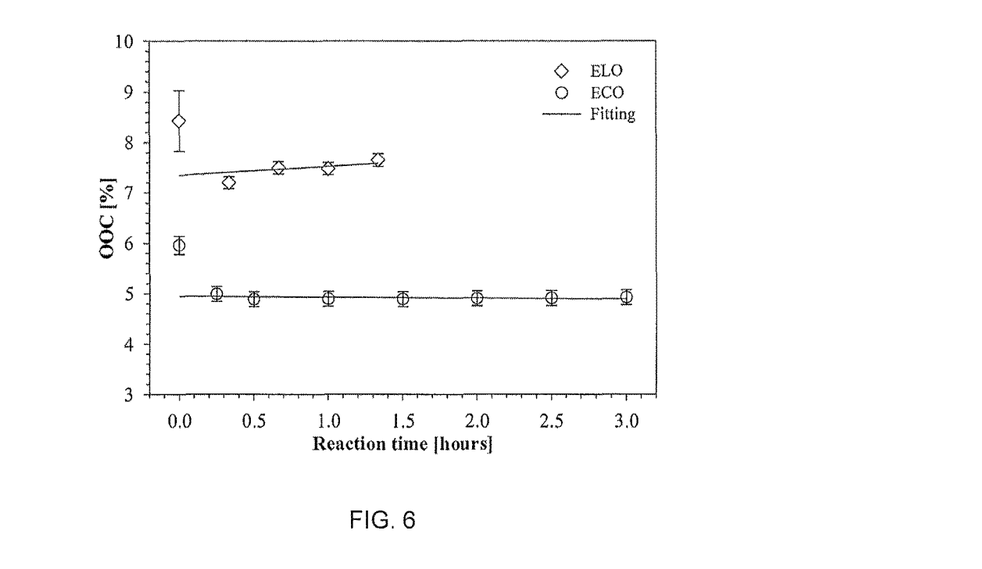
FIG. 6 is a graph showing oxirane oxygen content versus transesterification time for epoxidized flax oil, demonstrating that OOC values unchanged during transesterification reaction.

Optimization of the acid neutralization of sodium methoxide may be an important parameter toward obtaining a polyol having a light colour at the end of the process for applications such as, for example, coatings. This optimization of acid neutralization is also desirable to prevent epoxy ring opening process while neutralizing the sodium methoxide. As shown in FIG. 5 and Table 2, OHV reached a maximum at the end of the reaction, indicating that complete transesterification had occurred. As also shown in FIG. 6 the epoxy groups (OOC) of transesterified products of canola and flax oil epoxides were preserved and remain nearly unchanged during the transesterification reaction using sodium methoxide. Note that the higher OOC for the epoxidized canola oil and epoxidized flax oil is due to the differences in average molecular weights for epoxidized oil TAGs and epoxidized fatty acid alkyl esters. Linear fitting of experimental data in FIG. 6 was done using only epoxidized fatty acid alkyl esters.

Figure 7:
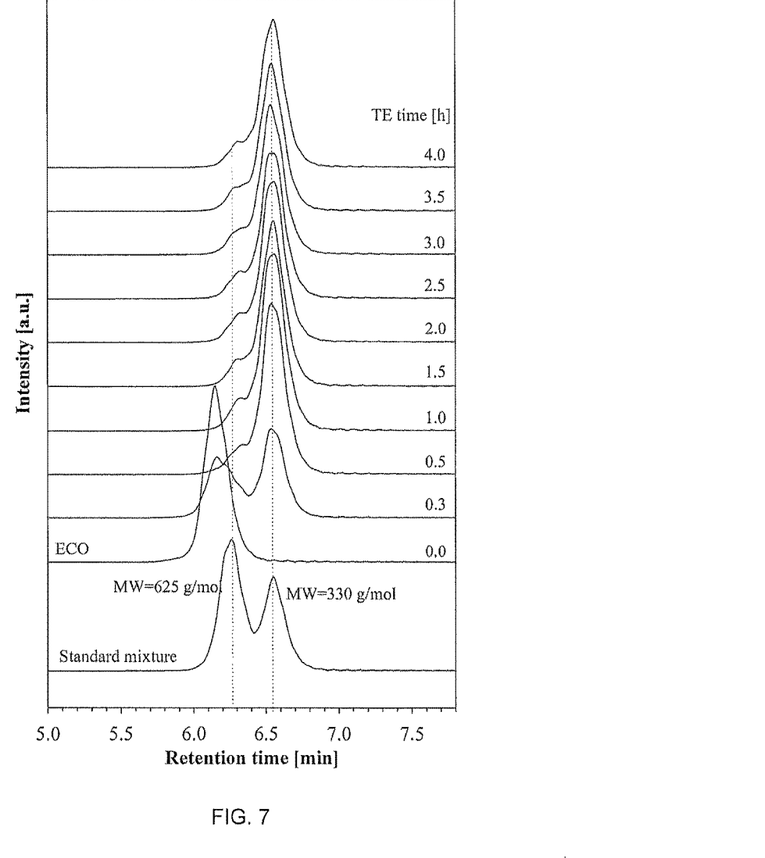
FIG. 7 is a graph demonstrating GPC (ELSD) chromatograms of the epoxidized canola oil and its transesterified (with 1,3-PDO) derivatives over transesterification time. The trace at 0 min shows GPC chromatogram of ECO. The trace labeled "Standard mixture" represents the chromatograms of distearin (MW-625 g/mol) and methyl-9,10-dihydroxystearate (MW-330 g/mol).

FIG. 7 is a graph showing GPC (ELSD) chromatograms of the epoxidized canola oil and its transesterified (with 1,3-PDO) derivatives over transesterification time. Sample at 0 min shows GPC chromatogram of epoxidized canola oil. This graph demonstrates the structural changes occurred during transesterification with 1,3-propanediol. As shown in FIG. 7 epoxidized TAG structure completely disappeared while no formation of new oligomeric structures were observed during transesterification reactions.

Example 3—Hydroxylation or Ring Opening

Figure 8:
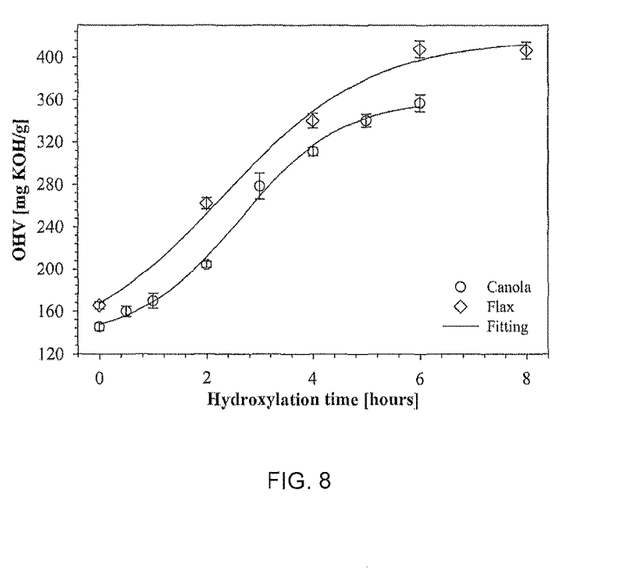
FIG. 8 is a graph showing hydroxyl value of the transesterified (with 1,3-PDO) derivatives of epoxidized canola (open circle symbols) and epoxidized flax (open diamond symbols) versus hydroxylation time (hours).

Transesterified products of epoxidized canola or epoxidized flax (1.0 kg) from Example 2 is loaded into the reactor and 1,3-propanediol (0.8 kg) was added. The temperature and agitation were set to 60° C. and 300 rpm, respectively. When the temperature of the mixture inside the reactor reached 60° C., Amberlyst™ 15 Dry (100 g, about 10 wt % to the product from Example 2) was transferred to the reactor and the reaction was continued for 6.0 hours. FIG. 8 is a graph showing the kinetics of the ring opening hydroxylation process for the transesterified products of epoxidized canola (open circle symbols) and epoxidized flax (open diamond symbols). The hydroxylated product was extracted by adding ethyl acetate (1.0 L) and washing four times with saturated salty water. Any remaining water was removed by adding sodium sulfate (0.25 kg). Ethyl acetate was removed using rotary evaporator under vacuum.

Example 4—Polyol

Table 3 compares the OHV (mg KOH/g) and viscosity (Pa·s) of polyols prepared according to the method of the present invention and a prior art process. Comparable data for flax, and the measured relative amounts of dimers and oligomers in the polyols are included. Using the method of the present invention, canola oil polyol exhibited an OHV of about 350 mg KOH/g and a low viscosity of about 1.6 Pa·s. The OHV comparison does not reflect the fact that in the polyol formed by the present invention, there is expected to be a much higher proportion of primary hydroxyl groups which are, for example, more reactive in polyurethane manufacture.

TABLE 3

OHV and viscosity of the new polyols and prior art FAME and TAG polyols from canola and flax oils

|  | OHV [mg KOH/g] | Viscosity [Pa · s] @25° C. | Dimers and Oligomers[1] [%] |
|---|---|---|---|
| New polyol (canola) | 350-360 | 1.6 ± 0.2 | 16 |
| Prior art FAME polyol (canola) | 260-270 | 0.4 ± 0.1 | 10 |
| Prior art TAG polyol (canola) | 270-280 | 3.5 ± 0.5 | 60-65 (TAG + oligomers) |
| New polyol (flax) | 400-410 | 7.5 ± 1.0[2] | 22 |
| Prior art FAME polyol (flax) | 330-340 | 1.2 ± 0.3 | 5 |
| Prior art TAG polyol (flax) | 300-310 | 13.5 ± 2.0 | — |

[1]Percentage of dimers and oligomers were calculated from the relative peak areas in GPC chromatograms.
[2]This viscosity measurement is believe to be anomalously high due to exceeding the optimal ring opening time Definitions and Interpretation As used herein, the term "fatty acid" means a carboxylic acid consisting of a hydrocarbon chain and a terminal carboxyl group. In addition, "fatty acid" refers to both free fatty acids and bound fatty acids. Bound fatty acids are fatty acid residues that are attached to other molecules, including any of those occurring as esters in fats and oils.

As used herein, the term "triacylglycerol" means an ester of three fatty acids and glycerol, which is the chief constituent of fats and oils.

As used herein, the term "free fatty acid" or "FFA" means a fatty acid which is not attached to any other molecule.

As used herein, the term "fatty acid methyl ester" or "FAME" means a type of fatty acid ester which is derived by transesterification of fat with methanol.

As used herein, the term "epoxidation" means a chemical reaction in which an oxygen atom is joined to an olefinically unsaturated molecule to form a cyclic, three-membered ether. The products of epoxidation are known as oxirane compounds or epoxides.

As used herein, the term "oxirane oxygen content" or "OOC" means the weight percent of oxirane oxygen in a molecule, and may be measured by methods described in ASTM D 1652.

As used herein, the term "hydroxyl value" or "OHV" means the number of milligrams of potassium hydroxide required to neutralize the acetic acid taken up on acetylation of one gram of a chemical substance that contains free hydroxyl groups, and may be measured by methods described in ASTM E222-10.

As used herein, the term "transesterification" means a process of exchanging the organic group R" of an ester with the organic group R' of an alcohol.

As used herein, the term "hydroxylation" means a chemical process that introduces a hydroxyl group (—OH) into an organic compound.

As used herein, the term "mono-alcohol" or "monohydric alcohol" means an alcohol having one hydroxyl group. As used herein, the term "diol" or "dihydric alcohol" means an alcohol having two hydroxyl groups. As used herein, the term "triol" or "trihydric alcohol" means an alcohol having three hydroxyl groups.

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a nonlimiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

REFERENCES

The following references are incorporated herein by reference (where permitted) as if reproduced in their entirety. All references are indicative of the level of skill of those skilled in the art to which this invention pertains.

Curtis, J.; Liu, G.; Omonov, T. and Kharraz, E. Polyol synthesis from fatty acids and oils. United States Patent Application Publication No. US 2013/0274494 A1, published Oct. 17, 2013.

Holser, R. A. (2008) Transesterification of epoxidized soybean oil to prepare epoxy methyl esters. *Industrial Crops and Products* 27(3):130-132.

What is claimed is:

1. A method for the preparation of polyols from an unsaturated triacylglycerol (TAG) oil comprising the steps of:
   (a) fully or partially epoxidizing the unsaturated TAG oil to obtain an epoxidized TAG oil;
   (b) transesterifying the epoxidized TAG oil using a diol and/or triol in the presence of a catalyst and a solvent, to produce a hydroxyalkyl esters of fatty acid epoxides; and
   (c) hydroxylating the transesterification product using a diol and/or triol and a catalyst to obtain a polyol.

2. The method of claim 1, wherein the unsaturated TAGs comprises canola oil, high oleic canola oil, sunflower oil, juvenile canola oil, flax oil, camelina oil, solin oil, yellow mustard oil, brown mustard oil, oriental mustard oil, palm oil olein, palm oil, palm kernel oil, soy oil, high erucic acid rapeseed oil, hemp oil, corn oil, olive oil, peanut oil, safflower oil, cottonseed oil or mixtures thereof, and the catalyst of step (c) comprises a solid acid catalyst.

3. The method of claim 2, wherein the unsaturated TAG oil comprises canola oil.

4. The method of claim 2 wherein the unsaturated TAG oil comprises flax oil.

5. The method of claim 1, wherein in step (a), the unsaturated TAG oil is epoxidized with an oxidizing agent and a carboxylic acid.

6. The method of claim 5, wherein the oxidizing agent comprises hydrogen peroxide and the carboxylic acid comprises formic acid.

7. The method of claim 5, wherein the unsaturated TAG is mixed with the oxidizing agent at a temperature of about 20° to about 40° C.

8. The method of claim 7, wherein the temperature is subsequently gradually increased to about 40° to about 60° C. as the acid is added slowly.

9. The method of claim 8, wherein the epoxidized unsaturated TAG is extracted using an organic solvent and dried.

10. The method of claim 1, wherein in step (b) and/or (c), the diol comprises 1,2-propane diol, 1,3-propane diol, 1,4-butane diol, ethylene glycol, glycerol, glycerol acetates, or mixtures thereof.

11. The method of claim 10, wherein the diol comprises 1,3-propane diol.

12. The method of claim 1, wherein in step (b) the catalyst comprises an alkoxide.

13. The method of claim 12, wherein the alkoxide comprises sodium methoxide.

14. The method of claim 1, wherein the epoxidized unsaturated TAG is mixed with the catalyst and the diol or the triol at a temperature of about 40° to about 70° C.

15. The method of claim 14, wherein the catalyst is neutralized by addition of a mineral acid, or a solid acid catalyst.

16. The method of claim 15, wherein the mineral acid comprises sulfuric acid and the solid acid catalyst comprises an acidic heterogeneous macroreticular ion exchange resin.

17. The method of claim 2, wherein in step (c), the solid acid catalyst comprises an acidic heterogeneous macroreticular ion exchange resin.

18. The method of claim 16, wherein the solid catalyst is added to a mixture of the epoxidized unsaturated TAG and the diol and/or triol once the mixture has reached a temperature of about 40° to about 60° C.

* * * * *